US 011273054B2

(12) United States Patent
Filipov

(10) Patent No.: US 11,273,054 B2
(45) Date of Patent: Mar. 15, 2022

(54) METHODS FOR HIP REPLACEMENT WITH ANTERIOR VERTICAL CAPSULE INCISION-MODIFIED ANATOMICAL DIRECT LATERAL APPROACH (VITOSHA APPROACH)

(71) Applicant: EKTA-Sofia Ltd., Sofia (BG)

(72) Inventor: Orlin Filipov, Sofia (BG)

(*) Notice: Subject to any disclaimer, the term of this patent is extended or adjusted under 35 U.S.C. 154(b) by 65 days.

(21) Appl. No.: 16/935,597

(22) Filed: Jul. 22, 2020

(65) Prior Publication Data

US 2022/0023068 A1 Jan. 27, 2022

(51) Int. Cl.
*A61B 17/16* (2006.01)
*A61F 2/32* (2006.01)
*A61F 2/46* (2006.01)
*A61B 17/02* (2006.01)

(52) U.S. Cl.
CPC ........ *A61F 2/4607* (2013.01); *A61B 17/1664* (2013.01); *A61F 2/32* (2013.01); *A61B 2017/0275* (2013.01)

(58) Field of Classification Search
CPC ...... A61F 2/4607; A61F 2/32; A61B 17/1664; A61B 17/0275
See application file for complete search history.

(56) References Cited

U.S. PATENT DOCUMENTS

| 9,622,758 | B2 | 4/2017 | Kelman |
| 10,456,274 | B2 | 10/2019 | Murphy et al. |
| 10,478,317 | B2 | 11/2019 | Chow |
| 10,603,173 | B2 | 3/2020 | Carr et al. |
| 2003/0229352 | A1 | 12/2003 | Penenberg |
| 2004/0092944 | A1 | 5/2004 | Penenberg |
| 2005/0081867 | A1 | 4/2005 | Murphy |
| 2013/0165941 | A1 | 6/2013 | Murphy |

OTHER PUBLICATIONS

Filipov, O. (2019), Surgical treatment of femoral neck fractures. Nova Science Publishers, Inc., New York, NY. ISBN: 978-1-53613-757-6. Monograph, Chapter 20, pp. 1-21.

*Primary Examiner* — Brian A Dukert
(74) *Attorney, Agent, or Firm* — Miller Law Group, PLLC

(57) ABSTRACT

The Modified anatomical direct lateral approach (Vitosha approach), a novel approach in hip arthroplasty, preserving the iliofemoral ligament and restoring the joint capsule, providing higher initial joint stability and easier rehabilitation without the need for post-operative patients' dislocation precautions is provided. The fascial incision curves along the posterior aspect of the greater trochanter and ends at its lower border, preventing a split of vastus lateralis muscle. The anterolateral periosteal layer which conjoins the gluteus medius and vastus lateralis muscles is sharply elevated from the greater trochanter. Gluteus medius muscle and the underlying gluteus minimus are split along its fibers and retracted anteriorly. A vertical capsular incision is made anterior to the femoral shaft, starting from the basicervical line and extending proximally along the longitudinal body axis, with the iliofemoral ligament fibers remained intact.

1 Claim, 3 Drawing Sheets

METHODS FOR HIP REPLACEMENT WITH ANTERIOR VERTICAL CAPSULE INCISION-MODIFIED ANATOMICAL DIRECT LATERAL APPROACH (VITOSHA APPROACH)

FIELD

The present document generally relates to a method for hip replacement with anterior vertical capsule incision—the Anatomical direct lateral approach for hip arthroplasty.

BACKGROUND

Despite hip arthroplasty superior clinical outcomes, the most of the standard contemporary approaches for hip arthroplasty are still associated with blood loss and the necessity for restricting patients activities during the early postoperative period due to impaired joint stability post-surgery (Tengborn et al., 2015; Lindman and Carlsson, 2018; Peters et al., 2015; Harkess and Crockarell, 2013).

In most contemporary hip arthroplasty approaches the blood loss can be significant, therefore tranexamic acid is routinely used in many institutions. Tranexamic acid substantially decreases perioperative blood loss, however, it cannot be administered to all patients, specifically those with high thrombotic risk or patients with a history of cardiovascular disease (Tengborn et al., 2015; Lindman and Carlsson, 2018).

With most contemporary hip arthroplasty approaches, due to impaired joint stability after surgery and the associated risk of joint dislocations, restrictions on patients' activities in their hip rotation, flexion and abduction/adduction are usually applied during the early postoperative period (e.g., use of pillows between the legs; prohibition to lie on one side) (Peters et al., 2015; Harkess and Crockarell, 2013).

Minimally invasive surgical techniques (MIS) provide less bleeding and less risk of dislocation compared to standard hip arthroplasty approaches (Yang et al., 2012). However, MIS techniques can be associated with risks of component malpositioning and early loosening due to limited operative exposure and suboptimal bone preparation (Bradley et al., 2010; Smith et al., 2011; Harkess and Crockarell, 2013).

Although blood loss is addressed by meticulous hemostasis, hypotensive anesthesia and tranexamic acid administration, the surgical technique remains paramount to minimize blood loss and achieve appropriate joint stability.

The Evolution of the Direct Lateral Approach

In 1954, McFarland and Osborne described a lateral approach based on the observation that the gluteus medius and vastus lateralis muscles act in direct functional continuity through the 'thick' periosteal junction over the greater trochanter. In their approach, the insertions of the gluteus medius and vastus lateralis muscles and their periosteal junction are detached with a thin bone shell from the lateral aspect of the greater trochanter and the combined muscle mass of the entire gluteus medius and vastus lateralis is retracted anteriorly. The tendon of the gluteus minimus is divided (cut) to expose the capsule. However, the detachment (cut) of gluteus minimus from the greater trochanter weakens the joint stability post-surgery.

In 1979, Bauer et al. described the 'transgluteal approach'. With this approach, the gluteus medius and vastus lateralis muscles are split along their fibers by blunt dissection and their anterior one-thirds are retracted anteriorly together with their periosteal junction after its 'sharp' elevation from the greater trochanter ('sharp elevation' means a detachment from the bone made by incision using a cautery diathermy knife or a scalpel or other instrument). The capsule is excised (thoroughly removed). Bauer describes that the intertrochanteric region is 'released' and gluteus minimus is retracted anteriorly. The gluteus minimus anterior retraction would not be possible without its described detachment (release) from the greater trochanter, which weakens the joint stability post-surgery.

Hardinge (1982) described the 'direct lateral approach to the hip'. With this approach, the anterior two-thirds of gluteus medius and the anterior part of vastus lateralis are sharply elevated together with their periosteal junction and displaced anteriorly. The tendinous insertion of the anterior portion of the gluteus minimus is separated (cut). A T-shaped incision of the capsule is made. Hardinge's approach allows improved joint access and avoids the need of a capsular excision, however, the dissections are quite extensive.

In 1984, McLauchlan described the Stracathro approach, where the joint is exposed by elevating anterior and posterior slices of the greater trochanter with the corresponding parts of the gluteus medius muscle attached proximally and the vastus lateralis distally. The gluteus minimus is split or detached from the greater trochenter. At closure, the capsule is sutured.

In 1986, Dall proposed an osteotomy of a large fragment involving the entire anterior-lateral part of the greater trochanter, made with the use of a Gigli saw. This technique is based on the fact that the larger parts of the gluteus medius and vastus lateralis muscles, as well as the whole of the gluteus minimus are attached to the anterior part of the greater trochanter. The large trochanteric fragment with the attached anterior halves of the vastus lateralis and gluteus medius muscles are retracted anteriorly together with the whole entity of the gluteus minimus. The anterior capsule is completely excised. A variation of this approach involves elevation of the anterior portion of the abductors with an attached thin wafer of bone from the anterior edge of the greater trochanter to facilitate their later repair and better abductor function (Harkess and Crockarell Jr, 2013).

In 1998, Mulliken et al. proposed sharp elevation of the anterior one-third of the gluteus medius and the anterior half of the vastus lateralis from the greater trochanter. The posterior part of gluteus medius is retracted posteriorly; a splitting of the gluteus minimus is performed under direct vision, and the anterior capsule is excised (removed). Mulliken et al. describes that 'a splitting of the gluteus minimus is performed', however only a splitting of gluteus minimus alone will not allow for an adequate access to the joint without detachment (cut) of its tendon anterior part from the greater trochanter.

In 2002, Pai was another who recommended for a sharp elevation of the anterior one-thirds of the gluteus medius and the vastus lateralis muscles, however, again with the gluteus minimus tendon detachment (cut) from the greater trochanter. The flap is retracted anteriorly and a T-shaped incision is made on the joint capsule. At closure, the preserved capsule is repaired.

In 2019, Filipov described the anatomical direct lateral approach (FIG. 2, FIG. 3, FIG. 4). With this approach, the skin incisions varies in length from 8 cm to 14 cm. The steps of the deep dissections and preparations are the following. 1. The fascial incision curves along the posterior aspect of the greater trochanter and ends at its lower border, preventing a split of vastus lateralis muscle. 2. A small bone fragment (bone patch) is osteotomized from the anterolateral aspect of the greater trochanter and is elevated and retracted anteriorly together with its covering periosteal layer which conjoins gluteus medius and vastus lateralis muscles (FIG. 3). This initiates the splitting of the gluteus medius and minimus proximally. 3. Using a gloved finger, the muscle split is continued bluntly between the anterior third and posterior two-thirds of both the gluteus medius muscle and the underlying tendinous part of gluteus minimus (FIG. 2), and their anterior thirds are retracted anteriorly together with the bone patch which is attached to them distally (FIG. 3, FIG. 4). 4. A vertical capsular incision is made anterior to the femoral shaft, starting from the basicervical line and extending proximally, and oriented along the longitudinal body axis, whereby the iliofemoral ligament fibers remain intact (FIG. 5). At closure, the capsule is restored by stitching. Next, the anterior muscular-periosteal flap with the bone patch is reinserted to the greater trochanter and fixed by stitching through drilled canals.

The present application describes the Modified anatomical direct lateral approach (Vitosha approach) in hip arthroplasty, aiming at minimizing operative trauma, decreasing blood loss, and optimizing joint stability. The better joint stability allows for easier rehabilitation without the need for dislocation precautions and patients' restrictions during the early post-operative period. Moreover, these benefits are achieved with a modified standard approach, thus avoiding all the risks associated with the minimally-invasive (MIS) approaches due to their limited joint exposure. The Modified anatomical direct lateral approach is a modification of the anatomical direct lateral approach (Filipov, 2019).

SUMMARY OF THE INVENTION

According to one aspect of the invention, there is provided a method of performing hip arthroplasty on a patient using a modified anatomical direct lateral approach, said method comprising preserving a iliofemoral ligament and restoring the joint capsule, by: making a fascial incision which curves along a posterior aspect of a greater trochanter of the patient, and ends at a lower border of said greater trochanter, thus preventing a split of a vastus lateralis muscle of the patient; next, elevating from the greater trochanter an anterolateral periosteal layer conjoining the gluteus medius and vastus lateralis muscles of the patient; continuing to elevate the anterolateral periosteal layer proximally by splitting both the gluteus medius muscle and the underlying gluteus minimus along fibers thereof, and anteriorly retracting anterior parts of said gluteus medius and said underlying gluteus minimus; without having performed any thochanteric osteotomy, making a vertical capsular incision in the hip joint capsule at a location anterior to the femoral shaft, starting from a basicervical line of a femoral neck of the patient and extending proximally along a longitudinal body axis of the patient, leaving the iliofemoral ligament fibers intact; and after placement of an endoprothesis in the patient, restoring the hip joint capsule, and reinserting an anterior muscular-periosteal flap of the patient by stitching thereof to the greater trochanter.

DETAILED DESCRIPTION

Figure 2:
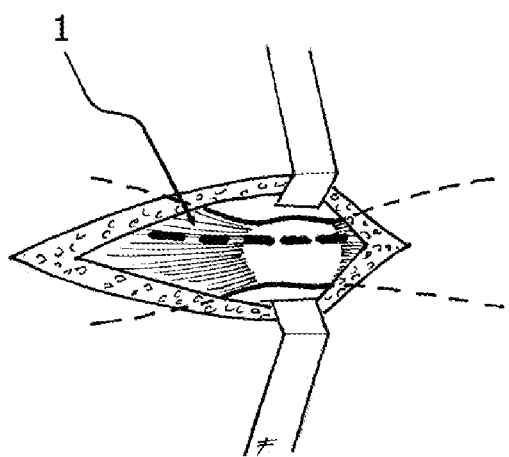
FIG. 2 illustrates the muscle splitting in the anatomical direct lateral approach. Gluteus medius muscle (1.), not entirely shown; The large dashed line shows the place of splitting of the gluteus medius and the underlying gluteus minimus (not shown) and the periosteal layer over the greater trochanter (the white area between gluteus medius and vastus lateralis). The fascial incision ends at the greater trochanter lower border level and the vastus lateralis muscle (not shown) is not split. The wound is retracted by retractors: one retractor is placed anterior and one posterior, however other instruments can also be used (Orientation in all figures: left—proximal (cranial); right—distal (caudal); upper—anterior; lower—posterior). The muscle splitting is the same in both the anatomical direct lateral approach (prior art) and the novel modified anatomical direct lateral approach (Vitosha approach), however with the modified anatomical direct lateral approach there is no trochanteric osteotomy, and the anterior part of gluteus minimus tendon is cut.
Figure 3:
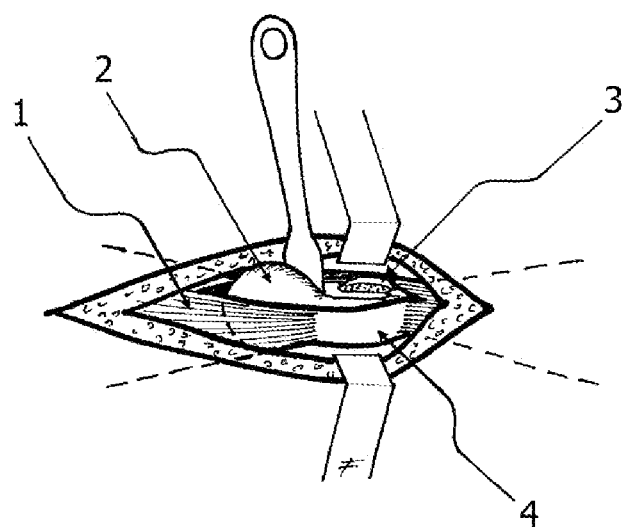
FIG. 3 illustrates the anatomical direct lateral approach (schematic representation). The splitted gluteus medius muscle (1.), not entirely shown (the splitted underlying gluteus minimus is not shown); After dislocation of the hip joint, the femoral head (2.) is shown located between the anterior and posterior parts of the splitted muscles; Osteotomized bone patch (3.), attached proximally to the splitted anterior parts of the gluteus medius and the underlying tendinous part of gluteus minimus (not shown) and attached distally to the vastus lateralis (its most proximal end is shown for didactic reasons, however during the operation it remains covered by the fascia). The wound is retracted by retractors: one retractor is placed anterior and one posterior, and a Hohmann retractor is shown placed anterior to the femoral neck, however other instruments can also be used (Orientation in all figures: left—proximal (cranial); right—distal (caudal); upper—anterior; lower—posterior). The muscle splitting is the same in both the anatomical direct lateral approach (prior art) and the novel modified anatomical direct lateral approach (Vitosha approach), however with the modified anatomical direct lateral approach there is no trochanteric osteotomy, and the anterior part of gluteus minimus tendon is cut.
Figure 5:
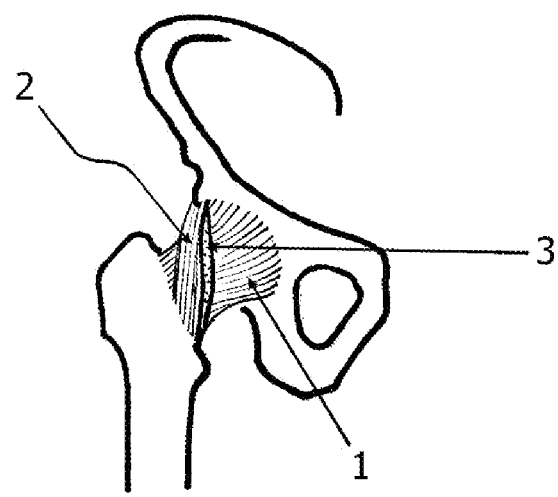
FIG. 5 illustrates the capsule incision in the anatomical direct lateral approach (schematic representation). Anterior joint capsule (1.); Iliofemoral ligament (2.), which is the strongest part of the joint capsule and an important joint stabilizing structure. The vertical capsular incision (3.) is made anterior to the femoral shaft and oriented along the longitudinal body axis, whereby the iliofemoral ligament fibers remain intact (the term 'vertical' means anatomically vertical). The capsule incision starts from the basicervical line distally, and extends proximally up to the proximal margin of the joint capsule. The capsule incision is the same in both the anatomical direct lateral approach (prior art) and the novel modified anatomical direct lateral approach (Vitosha approach), however with the modified anatomical direct lateral approach there is no trochanteric osteotomy, and the anterior part of gluteus minimus tendon is cut.

Disclosed herein is the Modified anatomical direct lateral approach (Vitosha approach) for hip arthroplasty, performed through an anterior vertical capsule incision, preserving the iliofemoral ligament and with full capsule restoration at closure, performed without any trochanteric osteotomy (FIG. 2, FIG. 5).

With the Modified anatomical direct lateral approach (Vitosha approach), the skin incision (or incisions) varies in length from 1 cm to 14 cm. After performing the fascial incision, which curves along the posterior aspect of the greater trochanter and ends at its lower border, preventing a split of vastus lateralis muscle (a "prior art" described in the anatomical direct lateral approach in 2019), the following innovative steps are performed, as follow.

1. The anterolateral periosteal layer which conjoins the gluteus medius and vastus lateralis muscles is sharply elevated from the greater trochanter, using a cautery pin or raspatory, or other instrument.

2. Using a cautery pin, the sharp dividing and elevation of the anterolateral periosteal layer is continued proximally by blunt splitting the gluteus medius muscle and the underlying tendinous part of gluteus minimus muscle along its fibers (FIG. 2).

3. Using cautery knife, the sharp elevation of the anterior parts of both the gluteus medius muscle and the underlying tendinous part of gluteus minimus runs along the curved shape of the anterior greater trochanter surface, which leads to detachment of the anterior tendon part of the split gluteus minimus from the bone.

4. The anterior parts of the two splitted muscles: the anterior part of gluteus medius muscle and the anterior part of the underlying gluteus minimus are retracted anteriorly without any osteotomy.

5. A vertical capsular incision is made anterior to the femoral shaft (FIG. 5), starting from the basicervical line and extending proximally, and oriented along the longitudinal body axis, whereby the iliofemoral ligament fibers remain intact. At this step, an innovative aspect is that this anterior vertical capsule incision is made without any previous thochanteric osteotomy.

The subsequent steps in this novel technique are the same as those, described in the anatomical direct lateral approach (2019).

The overall surgical procedure for the modified anatomical direct lateral approach (Vitosha approach), including the particularly novel steps recited in the preceding paragraphs, is therefore as follows.

1) With the patient in the lateral position, lateral skin incision (incisions) are made, with a length ranging from 1 cm to 14 cm, to end at the trochanteric base level distally.

The fascial incision curves along the posterior aspect of the greater trochanter and ends at its lower border without a split of the vastus lateralis.

Using cutting diathermy, a longitudinal incision is made along the periosteal tissue between the anterior end and the middle of the lateral surface of the greater trochanter (usually between the anterior one-third and the posterior two-thirds of the said surface). It outlines the place of the sharp elevation of the periosteal tissue from the anterolateral aspect of the greater trochanter (FIG. 2).

2) The anterolateral periosteal layer which conjoins the gluteus medius and vastus lateralis muscles is sharply elevated from the greater trochanter, using a cautery pin (knife) or raspatory, or other instrument (with the femur in external rotation). The elevated periosteal tissue layer is retracted anteriorly, which initiates the splitting of the gluteus medius and minimus proximally.

3) The gluteus medius and the underlying tendinous part of gluteus minimus are split along its fibers and retracted anteriorly. The initial splitting of gluteus minimus tendon is enabled by cauterization along its fibers, which cauterization, following the curved shape of the anterior greater trochanter surface leads to detachment of the anterior tendon part of the split gluteus minimus from the bone.

4) With the limb extended and externally rotated on the operating table, a straight longitudinal incision is made on the joint capsule along the anterolateral aspect of the femoral neck and head using the cautery pin. The capsule incision starts at the basicervical line just anterior to the femur and runs to the superior margin of the acetabulum (FIG. 5). The capsule incision is made along the longitudinal body axis, and not along the femoral neck axis, thus avoiding the need for a second transverse incision and preserving the iliofemoral ligament fibers. The preservation of the iliofemoral ligament is an innovative approach that improves early postoperative joint stability and makes rehabilitation easier.

5) This step depends on the particular patient condition that necessitated the surgical treatment:

A) In cases of femoral neck fractures, the Hohmann retractor is moved from the osteotomy site to in front of the femoral neck to retract the capsule, and the remaining part of the femoral neck is osteotomized using oscillating saw (usually at 8-10 mm above the lesser trochanter level) and the femoral head is extracted (usually using a corkscrew or a curved chisel).

B) Alternatively, in cases of osteoarthritis, the joint is dislocated by applying flexion, external rotation, and adduction, while pulling the head out of the acetabulum using a bone hook (or other instrument) placed beneath the femoral neck.

6) Hohmann retractors are placed over the anterior and posterior acetabular rims to retract the capsule (or other instruments or tag sutures) can be used.

7) The acetabular component of the endoprosthesis is placed in 0 to 15° acetabular anteversion with 30 to 50° (usually 40 to 45°) inclination.

8) The femoral component is positioned in 0 to 20° (usually 5 to 15°) femoral anteversion.

9) Joint stability is usually tested with the femur in its maximal external rotation during extension, and also in 45° flexion with adduction and maximal external rotation, but other tests can also be used if appropriate.

10) The wound is then closed in layers, usually starting with the joint capsule, but other sequence can also be used if appropriate. Two right-angled retractors are used to expose the capsule margins, but other instrument or instruments can also be used. The capsule is identified either visually or by the increased resistance, felt when the round needle passes through the capsule. The cut anterior capsule margin is stitched to the corresponding posterior capsule margin using usually two nonabsorbable stitches, placed at about 1 cm from each other, but other types of stitching can also be used. Thus the capsule is (almost) completely restored, both biologically—as an anatomical structure—and mechanically—as an important stabilizing structure.

11) The anteriorly retracted muscle-periosteal flap (consisting of the split anterior parts of gluteus medius and gluteus minimus and the anterior part of the periosteal layer from the anterolateral aspect of the greater trochanter) is now reinserted to the greater trochanter by stitching to the periosteal layer posterior part.

12) The fascia lata, subcutaneous tissue and skin are then closed in the usual manner.

Novel aspects of the Modified anatomical direct lateral approach (Vitosha approach), which are different from the anatomical direct lateral approach (2019), include the following.

1. The anterolateral periosteal layer which conjoins the gluteus medius and vastus lateralis muscles is sharply elevated from the greater trochanter, using a cautery pin or raspatory, or other instrument (there is no previous osteotomy on the greater trochanter and no bone fragment).

2. Using cauterization, the sharp elevation of the anterior parts of both the gluteus medius muscle and the underlying tendinous part of gluteus minimus runs along the curved shape of the anterior greater trochanter surface, which leads to detachment of the anterior tendon part of the split gluteus minimus from the bone (the anterior tendon part of gluteus minimus is not attached to any bone fragment).

3. There is no bone fragment attached to the retracted anterior parts of gluteus medius and the underlying gluteus minimus.

4. A vertical capsular incision is made anterior to the femoral shaft (FIG. 5), starting from the basicervical line and extending proximally, and oriented along the longitudinal body axis, without any previous trochanteric osteotomy.

Both, the Modified anatomical direct lateral approach (Vitosha approach) and the anatomical direct lateral approach (2019) differ from the other direct lateral approach techniques described in the literature in terms of the following aspects.

1) The fascial incision ends at the lower border level of the greater trochanter.

2) The vastus lateralis muscle is not split.

3) The most important and innovative is the capsular incision: a single, vertical capsular incision anterior to the femoral shaft is made, oriented along the longitudinal body axis (not along the femoral neck axis).

4) The iliofemoral ligament fibers are preserved intact, because the capsule incision is parallel to the iliofemoral ligament fibers.

5) At closure, the joint capsule is restored by stitches and it is very strong because of the vertical orientation of the capsule incision. The capsule preservation and stitching has been described in other techniques (prior art), but it is very rarely seen in other hip arthroplasty techniques, and it is innovative in this context because it is combined with the vertical shape of the capsule incision.

6) The anterior abductor flap is shorter, involving only the retracted anterior parts of the gluteus medius and gluteus minimus muscles and the periosteal layer distally to them (with or without an osteotomized bone patch attached to it), without involving the vastus lateralis muscle. The shorter abductor flap provides much better stability after its reinsertion to the greater trochanter.

The first few steps of the muscle dissections are based on the fact that large parts of the gluteus medius and vastus lateralis muscles and the entire gluteus minimus are attached to the anterior part of the greater trochanter, as described by Desmond Dall (1986).

Nonetheless, the novel Modified anatomical direct lateral approach (Vitosha approach) and the anatomical direct lateral approach (2019) differ from the technique of Dall (1986) in the following aspects.

1) The gluteus medius muscle and the underlying tendinous part of gluteus minimus are split and their anterior parts (one-thirds or less) are retracted anteriorly (in contrast to Dall's technique, where the entire gluteus minimus muscle is mobilized anteriorly remaining attached to the massive osteotomized bone fragment);

2) A single vertical capsular incision is made anterior to the femoral shaft along the longitudinal body axis, parallel to the iliofemoral ligament, therefore the iliofemoral ligament fibers remain intact (FIG. 5) (with Dall's technique the anterior capsule is removed (excised)).

Figure 1:
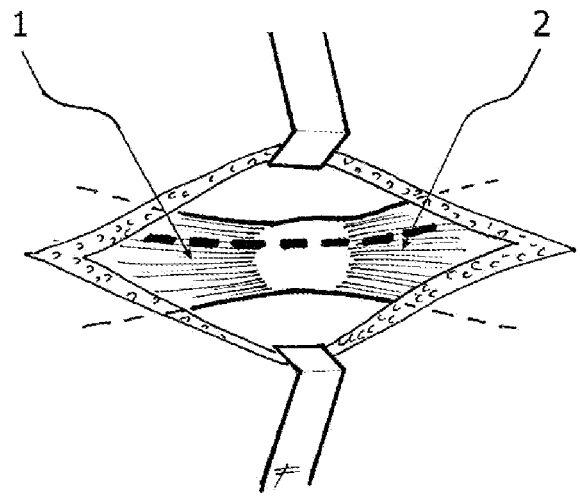
FIG. 1 illustrates the standard direct lateral approach (prior art), (schematic representation). Gluteus medius muscle (1.), not entirely shown; Vastus lateralis muscle (2.), not entirely shown; The large dashed line shows the place of splitting of the gluteus medius and the underlying gluteus minimus (not shown) and the vastus lateralis muscle and the conjoining periosteum over the greater trochanter (the white area between gluteus medius and vastus lateralis). The wound is retracted by right-angled retractors: one placed anterior and one posterior. (Orientation in all figures: left—proximal (cranial); right—distal (caudal); upper—anterior; lower—posterior).
Figure 4:
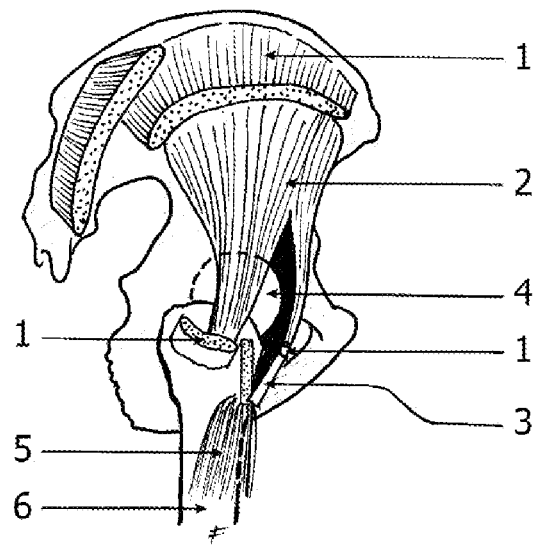
FIG. 4 illustrates the anatomical direct lateral approach. The osteotomized small bone fragment (bone patch) is retracted anteriorly with the splitting of the gluteus medius and minimus muscles (schematic representation). Gluteus medius muscle (1.), not entirely shown; Gluteus minimus muscle, splitted (2.); Osteotomized bone patch (3.); Femoral head (4.); Vastus lateralis muscle (5) and Femoral shaft (6)—not entirely shown. The muscle splitting is the same in both the anatomical direct lateral approach (prior art) and the novel modified anatomical direct lateral approach (Vitosha approach), however with the modified anatomical direct lateral approach there is no trochanteric osteotomy, and the anterior part of gluteus minimus tendon is cut.

3) The fascial incision curves along the posterior aspect of the greater trochanter and ends at its lower border, which prevents of distal split of the vastus lateralis muscle (FIG. 2, FIG. 4), in contrast to Dall's technique where the fascial incision extends distally of the greater trochanter and the vastus lateralis muscle is split (FIG. 1).

4) The entire joint capsule is preserved (no capsule parts are excised), in contrast to the Dall's technique.

5) Particularly, with the anatomical direct lateral approach (2019) a small bone patch is osteotomized (in contrast to Dall's technique where a large bone fragment is osteotomized);

In U.S. Pat. No. 10,478,317 there is described that the joint capsule incision is proximal from the tip of the greater trochanter: 'A main incision is initiated at a point being a projection of a tip of a greater trochanter and extends proximally' and 'An inline capsulotomy is performed'. In US Patent Application #20050081867 is described: 'making a superiorly positioned incision' (claim 5); and later in the same document, the 'superior incision' is further described (in claim 9) as 'performing vertical capsulotomy on the hip joint and placing retractors inside the hip joint on both sides of the femoral neck while said femoral head is within the acetabulum'.

In contrast to the capsule incisions described in the above cited patents, which incisions are oriented vertical but they are made superior (proximal) to the greater trochanter, with the Modified anatomical direct lateral approach and the anatomical direct lateral approach (2019), the capsule incision is made also vertical (longitudinal, along the body axis) but it is placed anterior to the femur, which is innovative and is a substantial difference with the cited patents, and is very important for the preservation of the iliofemoral ligament and for the joint stability.

Previous studies have shown that restrictions in the immediate post-operative period are not necessary when using direct anterior minimally invasive approach (Peak et al., 2005). However, such minimally invasive surgical (MIS) techniques can be related to risks of component malpositioning and early loosening due to limited exposure (Bradley et al., 2010; Smith et al., 2011; Harkess and Crockarell, 2013).

Previous studies have shown that dislocation precautions are unnecessary when using conventional anterolateral approaches in THA (Peak et al., 2005). However, due to the limited access provided with all anterolateral approaches, they are associated with the need to cut the anterior third of gluteus medius insertion and to cut the entire tendon of gluteus minimus, leading to deterioration of the abductor mechanism and risk of limping.

Advantages of the Novel Technique

With both the Modified anatomical direct lateral approach (Vitosha approach) and the anatomical direct lateral approach (2019), there are numerous advantages, including the following.

1) The hip joint is accessed through a single vertical capsular incision anterior to the femur with preservation of the iliofemoral ligament, thus resulting in high joint stability post-operatively and allowing optimal restoration of the soft tissue anatomy.

2) In comparison to the anterior or most of the anterolateral approaches, this modified approach enables better access to the hip joint for preparation of the bone surfaces and for implant positioning; and similar or better access compared to the other direct lateral approaches. However, it substantially avoids the risk of abductor weakness and limping post-surgery associated with most of the direct lateral approaches, due to its secure reattachment of the anterior abductor flap and especially when bone-to-bone union is achieved when the anatomical direct lateral approach is used.

3) Also, in comparison to the anterior, anterolateral or the other direct lateral approaches, the risk of anterior joint dislocation is substantially reduced due to the iliofemoral ligament preservation.

4) As compared to the posterior, posterolateral or the other direct lateral approaches, this technique is associated with less blood loss, shorter operative time, substantially less dissection and less operative trauma.

5) In comparison to the posterior and posterolateral approaches, due to preservation of the posterior joint capsule untouched as in other direct-lateral, anterolateral or anterior approaches, the posterior dislocation risk is substantially reduced.

6) Due to preservation of all joint stabilizing structures, this technique provides a much better initial joint stability during the early post-operative period and minimizes the risk of dislocations, and thereby it allows for easier and safer rehabilitation as in the anterior minimally-invasive (MIS) approaches, but avoiding the risks of malpositioning of the implant components and its early loosening due to the suboptimal bone preparation associated with all MIS-techniques. Patients are encouraged to exercise activities within the normal range of motion and without special patient's restrictions or dislocation precautions in their early postoperative period (except excessive flexion).

7) Both the Modified anatomical direct lateral approach and the anatomical direct lateral approach techniques are safe surgical procedures suitable for standardization, and easy to perform with only one assistant.

The anatomical direct lateral approach (2019) has been applied since 2016, demonstrating excellent clinical results (Filipov, 2019). During the follow-up, no cases of dislocations or other early complications were registered, and a faster patient recovery was observed. The registered blood loss is on average 50% less compared to most of the standard direct lateral approach modifications, particularly in comparison to the direct lateral approach by Mulliken et al., 1998. The Modified anatomical direct lateral approach is a further improvement of the anatomical direct lateral approach, made by its author.

Disadvantages. No disadvantages with the anatomical direct lateral approach (2019) have been observed during its clinical application since 2016. No disadvantages with the novel Modified anatomical direct lateral approach are expected.

In conclusion, the Modified anatomical direct lateral approach is a promising procedure, a further improvement of the anatomical direct lateral approach—which is a standardized and safe procedure, it results in improved joint stability, less bleeding and less operative trauma, and the faster recovery is achieved without patients' restrictions and avoiding the risks of the MIS techniques.

CITED REFERENCES

Each Incorporated Herein by Reference in its Entirety

1. Bauer, R., Kerschbaumer, F., Poisel, S., Oberthaler, W. (1979). The transgluteal approach to the hip joint. Arch Orthop Trauma Surg, 95(1): 47-49.
2. Bradley, P., Graw, M. D., Steven, T., Woolson, M. D., Heather, G., et al. (2010). Minimal Incision Surgery as a Risk Factor for Early Failure of Total Hip Arthroplasty. Clin Orthop Relat Res, 468: 2372-2376.
3. Dall, D. (1986), Exposure of the hip by anterior osteotomy of the greater trochanter. J Bone Joint Surg, 68B: 382-385.
4. Filipov, 0. (2019), Surgical treatment of femoral neck fractures. Nova Science Publishers, Inc., New York, N.Y. ISBN: 978-1-53613-757-6. Monograph.
5. Frndak, P. A., Mallory, T. H., Lombardi, A. V, Jr. (1993). Translateral surgical approach to the hip: the abductor split. Clin Orthop, 295: 135-140.
6. Hardinge, K. (1982). The direct lateral approach to the hip. J Bone Joint Surg, 64(B): 17-18.
7. Harkess, J., Crockarell, J. Jr. (2013). Arthroplasty of the hip, in Canale, S. T., Beaty, J. H., eds: Campbell's Operative Orthopedics (ed 12, vol. 1, pp 159-300). Philadelphia, Pa., Mosby Elsevier.
8. Jolles, B. M., Bogoch, E. R. (2004). Surgical approach for total hip arthroplasty: direct lateral or posterior? J Rheumatol, 31(9): 1790-1796.
9. Learmonth, I. D., Allen, P. E. (1996). The omega lateral approach to the hip. J Bone Joint Surg, 78(B): 559-561.
10. Lindman, I. S., Carlsson, L. V. (2018). Extremely low transfusion rates: contemporary primary total hip and knee arthroplasties. J Arthroplasty, 33: 51-54.
11. McFarland, B., Osborne, G. (1954). Approach to the hip: a suggested improvement on Kocher's method. J Bone Joint Surg, 36(B): 364-367.
12. Mclauchan, J. (1984). The Stracathro approach to the hip. J Bone Joint Surg, 66B: 30-31.
13. Mulliken, B. D., Rorabeck, C. H., Bourne, R. B., Nayak, N. (1998). A modified direct lateral approach in total hip arthroplasty. J Arthroplasty, 13(7): 737-747.
14. Pai, V. S. (2002). A modified direct lateral approach in total hip arthroplasty. J Orthop Surg, 10(1): 35-39.
15. Peters, A., Tijink, M., Veldhuijzen, A., et al. (2015). Reduced patient restrictions following total hip arthroplasty: study protocol for a randomized controlled trial. Trials, 16:360. doi: 10.1186/s 13063-015-0901-0.
16. Smith, T. O., Blake, V., Hing, C. B. (2011). Minimally invasive versus conventional exposure for total hip arthroplasty: a systematic review and meta-analysis of clinical and radiological outcomes. Int Orthop, 35(2): 173-184.
17. Tengborn, L., Blomback, M., Berntorp, E. (2015). Tranexamic acid—an old drug still going strong and making a revival. Thromb Res, 135(2): 231-242.

18. Yang, B., Li, H., He, X, Wang, G., Xu, S. (2012). Minimally Invasive Surgical Approaches and Traditional Total Hip Arthroplasty: A Meta-Analysis of Radiological and Complications Outcomes. PLoS ONE, 7(5): e37947. doi:10.1371/journal.pone.0037947.

The invention claimed is:

1. A method of performing hip arthroplasty on a patient using a modified anatomical direct lateral approach, said method comprising preserving a iliofemoral ligament of the patient and restoring a hip joint capsule of the patient, by:

making a fascial incision which curves along a posterior aspect of a greater trochanter of the patient, and ends at a lower border of said greater trochanter, thus preventing a split of a vastus lateralis muscle of the patient;

next, elevating from the greater trochanter an anterolateral periosteal layer which conjoins gluteus medius and vastus lateralis muscles of the patient;

continuing to elevate the anterolateral periosteal layer proximally by splitting both the gluteus medius muscle and an underlying gluteus minimus along fibers thereof, and anteriorly retracting anterior parts of said gluteus medius and said underlying gluteus minimus;

without having performed any thochanteric osteotomy, making a vertical capsular incision in the hip joint capsule at a location anterior to a femoral shaft of the patient, starting from a basicervical line of a femoral neck of the patient and extending proximally along a longitudinal body axis of the patient, leaving the iliofemoral ligament fibers intact; and after placement of an endoprosthesis in the patient, restoring the hip joint capsule, and reinserting an anterior muscular-periosteal flap of the patient by stitching thereof to the greater trochanter.

* * * * *